(12) United States Patent
Wabel et al.

(10) Patent No.: US 12,178,947 B2
(45) Date of Patent: Dec. 31, 2024

(54) APPARATUS CONTAINING DIALYSIS SOLUTION OR DIALYSIS SOLUTION CONCENTRATE

(71) Applicant: Fresenius Medical Care Deutschland GmbH, Bad Homburg (DE)

(72) Inventors: Peter Wabel, Rosbach (DE); Robert Berlich, St. Wendel (DE); Marcus Breuninger, Bad Homburg (DE); Birgit Staude, Pfungstadt (DE); Matthias Rau, Wiesbaden (DE); Klaus Wolf, Muedesheim (DE)

(73) Assignee: FRESENIUS MEDICAL CARE DEUTSCHLAND GMBH, Bad Homburg (DE)

( * ) Notice: Subject to any disclaimer, the term of this patent is extended or adjusted under 35 U.S.C. 154(b) by 1137 days.

(21) Appl. No.: 16/971,456

(22) PCT Filed: Feb. 14, 2019

(86) PCT No.: PCT/EP2019/053641
§ 371 (c)(1),
(2) Date: Aug. 20, 2020

(87) PCT Pub. No.: WO2019/162178
PCT Pub. Date: Aug. 29, 2019

(65) Prior Publication Data
US 2020/0397970 A1 Dec. 24, 2020

(30) Foreign Application Priority Data
Feb. 21, 2018 (DE) .................. 10 2018 103 937.9

(51) Int. Cl.
*A61M 1/28* (2006.01)
*A61M 1/16* (2006.01)
*A61M 39/22* (2006.01)

(52) U.S. Cl.
CPC ............ *A61M 1/28* (2013.01); *A61M 1/1668* (2014.02); *A61M 39/223* (2013.01)

(58) Field of Classification Search
CPC .......... A61M 1/28–288; A61M 39/165; A61M 2039/1066
See application file for complete search history.

(56) References Cited

U.S. PATENT DOCUMENTS 4,298,001 A * 11/1981 Hargest, III ........ A61M 39/146
604/905
4,950,230 A * 8/1990 Kendell ............... A61M 1/28
604/32

(Continued)

FOREIGN PATENT DOCUMENTS

DE         19520916     1/1997
JP         2007-44562     2/2007

(Continued)

*Primary Examiner* — Courtney B Fredrickson
(74) *Attorney, Agent, or Firm* — Jacobson Holman PLLC

(57) ABSTRACT

The present invention relates to an apparatus for providing a dialysis solution and preferably a peritoneal dialysis solution comprising a reception container that can accommodate a solution volume that is intended for at least two treatments, wherein the apparatus has a plurality of extraction ports for extracting the dialysis solution from the reception container.

7 Claims, 4 Drawing Sheets

(56) References Cited

U.S. PATENT DOCUMENTS

Figure 1:
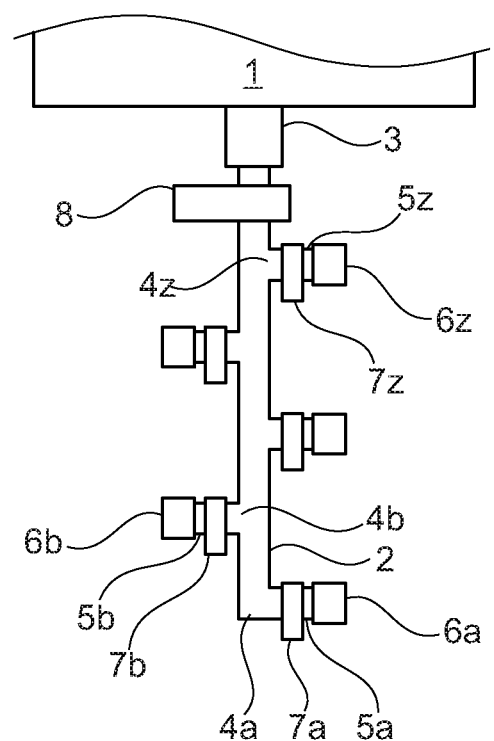

| | | | | |
|---|---|---|---|---|
| 5,722,947 | A | * | 3/1998 | Jeppsson ................ A61M 1/28 128/DIG. 13 |
| 7,559,913 | B1 | * | 7/2009 | Jeppsson ............... A61M 1/281 604/29 |
| 2014/0276373 | A1 | | 9/2014 | Minkus |
| 2017/0049955 | A1 | * | 2/2017 | Uber, III ............. A61M 5/1408 |

FOREIGN PATENT DOCUMENTS

| JP | 2017-505669 | 2/2017 |
|---|---|---|
| WO | WO2010/096657 | 8/2010 |

* cited by examiner

APPARATUS CONTAINING DIALYSIS SOLUTION OR DIALYSIS SOLUTION CONCENTRATE

The invention relates to an apparatus containing a dialysis solution or a dialysis solution concentrate, preferably for use in peritoneal dialysis, comprising a reception container that can accommodate a solution volume which is intended for at least two treatments.

It is in particular customary in the field of peritoneal dialysis to provide the patient with solution bags that are filled with a dialysis solution suitable for the patient. The patient then connects these solution bags to an inflow hose, i.e. to the patient catheter, independently or with the aid of trained medical personnel to fill the peritoneum with the solution. The dialysis solution typically has to be transported to the patient's home in the fully prepared state.

It would be desirable to store a solution volume for a plurality of treatments in a container, for example a bag, in order thus to be able to reduce waste and to be able to simplify the manufacturing process and the quality control such that fewer containers have to be filled. The transportation and the handling can also be simpler for the patient under certain circumstances if only one container has to be handled.

The idea is already disclosed in WO 2010/096657 A1 to fill a container with a volume of peritoneal dialysis solution that is intended for a plurality of treatments. A metering bag is there connected between the large container and the patient to simplify the metering of the correct amount of liquid for a treatment. However, there have previously been no suitable measures to ensure the sterility of the extraction port if dialysis solution should be extracted several times from the same container.

It is the object of the invention to find a suitable connection concept for the multiple extraction of dialysis solution from the same reception container in which the sterility of the extraction port is also reliably ensured in particular after the first extraction and after further extractions.

Against this background, the invention relates to an apparatus containing a dialysis solution or a dialysis solution concentrate, preferably for use in peritoneal dialysis, comprising a reception container that can accommodate a solution volume that is intended for at least two treatments, wherein the apparatus has a plurality of extraction ports for extracting the dialysis solution from the reception container. A treatment is understood in connection with peritoneal dialysis as a complete or partial filling of the abdomen. An extraction port is understood in the given context as an interface for the direct or indirect connection of the line leading into the abdomen of the patient, i.e. to the patient catheter. The extraction port can, for example, be provided with a Luer connector for this purpose.

A fresh extraction port can be used for each of a plurality of extractions of dialysis solution from the reception container due to the plurality of ports.

The reception container can have a volume of more than 5 liters, more than 10 liters, or even more than 20 liters. The volume typically required as part of a single treatment is in an order of magnitude of approximately 2 liters. The number of ports can be coordinated with the size of the reception container. The apparatus can, for example, have at least one extraction port per two liters of volume of the reception container.

In addition to the ports for extracting the dialysis solution, the reception container typically has a filling port for filling with dialysis solution.

The reception container can be a flexible bag or a rigid receptacle. A pressure equalizing valve can be provided in the case of a rigid receptacle. It can be a flexible, and preferably elastic bag that is stored in a rigid receptacle. On the filling of the bag, such a bag ideally largely fills the space of the surrounding rigid receptacle. Such a bag-in-box packaging has the advantage that the inner bag, that is typically formed as a disposable element, is protected from mechanical influences by the outer packaging. The mechanical robustness of the solution bag, here an inner bag, has reduced importance with respect to previously known solutions, whereby a material-saving and less expensive design is made possible. The cost saving and the saving of waste are in particular considerable due to the fact that the solution bags are typically disposable products.

The receptacle can be transparent or can have a transparent inspection window. Filling level marks can optionally be provided. The apparatus can optionally have a metering container that is arranged between the extraction port and the reception container to simplify the metering of the correct quantity of liquid for one treatment.

Provision is made in an embodiment that a valve and a drainage port is associated with each extraction port. Each extraction port can thus also be used for a draining procedure. Examples of suitable valves include rotary valves or 3/3-way valves. After connecting the line leading into the abdomen of the patient to the extraction port, the previously closed valve can first be adjusted or the valve can remain adjusted such that consumed dialysis solution flows off through the drainage port or through a drainage line connected thereto. The valve can then be adjusted such that fresh dialysis solution can flow from the reception container into the abdomen of the patient. A valve position can optionally also be adopted for venting the line in which a flow of dialysis solution from the reception container into the drainage port or into a drainage line connected thereto is made possible.

Provision is made in an embodiment that the apparatus has a main extraction line that is connected to the reception container and from where a plurality of individual extraction lines with extraction ports lead off. Provision can alternatively or additionally be made that respective closing means are arranged in the single extraction lines and the single extraction lines can be closed by them. The closing means can, for example, be clamps with which the respective line can be pinched off. Provision is made in an embodiment that the closing means, and preferably clamps, are configured such that the respective line can be irreversibly closed. Provision is made in an embodiment that the closing means are configured such that they close automatically on or after a decoupling of the single extraction line from the patient. In an embodiment, the closing means are configured such that a repeat opening of the used single extraction line is impossible.

Provision is made in an embodiment that the single extraction lines branch off from the main extraction line at different branch points that are distributed over the length of the main extraction line. The line system comprising the main extraction line and the single extraction lines has a tree structure in this embodiment, with the main extraction line corresponding to the trunk and the single extraction lines corresponding to the branches. A single line can be associated with each extraction port.

Provision is made in an embodiment that respective closing means are arranged in the main extraction line between branch points of the single extraction line that follow one another and with which the main extraction line can be closed. The closing means can be configured as described in more detail above.

Provision can be made in use to use that extraction port for the first liquid extraction that is seated at the last single extraction line, i.e. at the single extraction line furthest remote from the reception container. After ending this procedure, the respective single extraction line can be closed using a closing means. e.g. a clamp, a valve, or a faucet. Alternatively, the main extraction line can be closed at a point between the branches of the last and second-to-last single extraction lines using a closing means. On the second liquid extraction, the second-to-last extraction port can then be used and subsequently it can also be decoupled by closing the single extraction line or the main extraction line. This procedure can be repeated until the last extraction port at the last single extraction line, i.e. the single extraction line closest to the reception container, is used or until the entire dialysis solution in the reception container has been used up. A decoupling at the main extraction line can have the advantage that less dead volume arises.

Provision is made in an embodiment that the main extraction line opens into a distributor and the single extraction lines lead off from the distributor in star shape. The distributor can have a switch that is configured such that the release of an individual single extraction line is always only possible and such that only such a single extraction line can be released that has not yet previously been used. An example for a suitable switch includes a rotary switch that can only be turned in one direction.

In an embodiment variant, a connection mechanism can be provided at the lead side end of the main extraction line and is configured to be able to decouple the line system in its entirety from the reception container. Either the reception container or the line system can thus be reused, for example.

The main extraction line and/or the individual extraction lines can optionally have check valves as an additional contamination barrier.

Provision is made in an embodiment that the apparatus has an extraction line at which the extraction ports are connected in series, with provision preferably being made that the extraction line is divided into a plurality of decouplable sectors and an extraction port is arranged in each of the sectors. Closing means as described above can be arranged in the individual sectors to be able to decouple the sectors. The sectors can be connected to one another using connectors that have break points to be able to separate a sector having a used extraction port. The break points are preferably configured such that the passage is closed on the separation.

Provision is made in an embodiment that the extraction ports are individually sealed by airtight sheaths, with provision preferably being made that a number of sheaths corresponding to the number of extraction ports is present, with an innermost sheath surrounding an extraction port and every further sheath surrounding the existing sheath and a further extraction port. Suitable sheaths include, for example, plastic bags, caps or the like. Provision can be made that the sheaths follow the principle of a Russian doll. If the outermost sheath is opened, an extraction port and the next sheath are released which seals all further extraction ports. If this next sheath is opened, a further extraction port and the next-but-one sheath are released, and so on. The last extraction port is only released after the opening of the innermost sheath. The risk of confusing already used ports and fresh ports can be minimized by this kind of sealing. In the case of the line system presented above having a main extraction line and single extraction lines in a tree structure, the last extraction port at the last, single extraction line, i.e. the single extraction line closest to the reception container can be surrounded by all the sheaths and the first extraction port at the first single extraction line, i.e. the single extraction line furthest away from the reception container, can be surrounded only by the outermost sheath.

Provision is made in an embodiment that the extraction ports have a security against double use that irreversibly closes the extraction port after use. The security against double use can, for example, comprise a movable sleeve that can be moved from an open position into a closed position and that blocks the extraction port in the closed position. The sleeve can, for example, be configured such that it can be displaced in an axial direction of the port from an open position into a closed position. Provision can be made that the closed position is irreversible, i.e. that the sleeve can no longer be displaced from the closed position back into the open position. This blocking can, for example, be implemented by a latch projection and a latch nose. An unwanted multiple use of the same port can thus be effectively avoided. The sleeve can, for example, be preloaded against the closed position so that it is automatically moved into the closed position on a breaking open of a holding element. The holding element can be configured such that it is broken open on a coupling of the line leading into the abdomen of the patient. The sleeve is then held for so long by the patient line as the latter is connected. The sleeve closes irreversibly on extraction.

In an embodiment of the invention, the container does not contain any ready-to-use concentrate, but only a concentrate. The ready-to-use dialysis solution can be prepared on site by filling the container with purified sterile water, for example from a reverse osmosis plant. In such an embodiment, the container also has an infeed for liquids, with the infeed preferably being closable. The concentrate can be presented freely in the container or in a separate compartment. A plurality of different concentrates can also be presented in a plurality of compartments. A fluid communication between the concentrate compartments and a mixing compartment can be established by breaking open by a break connection. Peelable weld seams are, for example, suitable as a break connection for the case that the container is a film bag.

Figure 2:
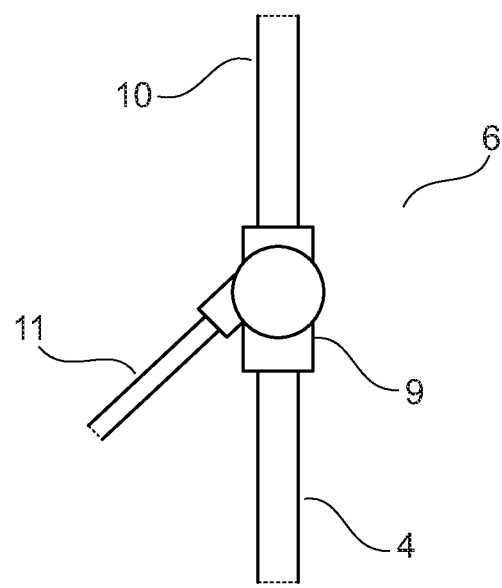
Figure 3:
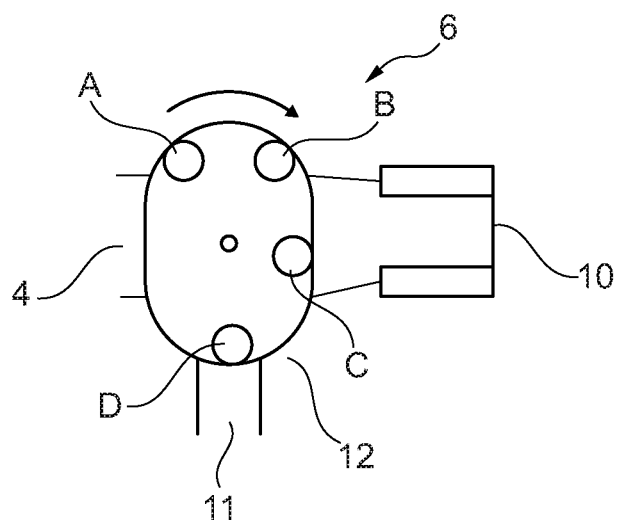
Figure 5:
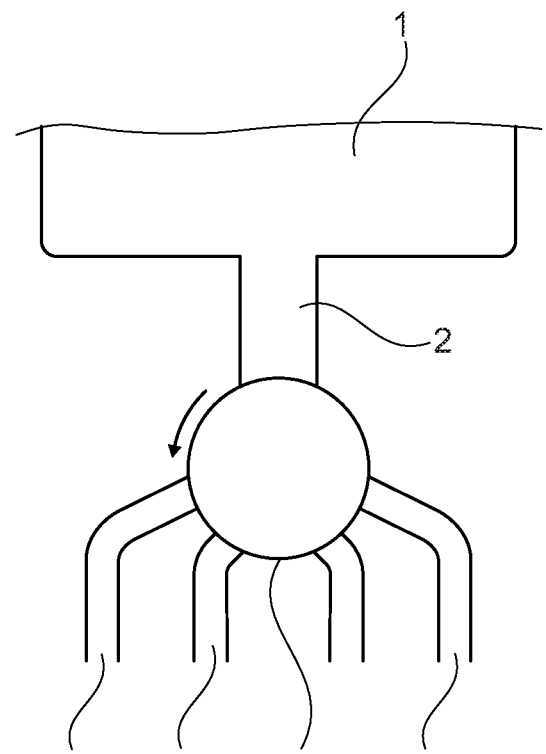
Figure 6:
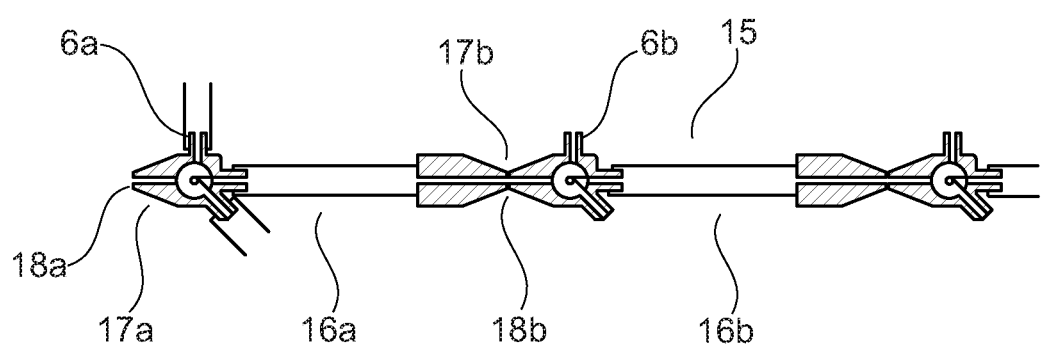

Further details and advantages of the invention result from the embodiments described in the following with reference to the Figures. There are shown in the Figures:

FIG. 1: an apparatus in accordance with the invention with a line system comprising a main extraction line and a plurality of single extraction lines in a tree structure;

FIG. 2: a variant of an extraction port with a drainage port and a 3-way valve;

FIG. 3: a variant of an extraction port with a drainage port and a rotary switch;

FIG. 4: the apparatus of FIG. 1 with a Matryoschka sheathing of the extraction ports;

FIG. 5: an apparatus in accordance with the invention with a line system comprising a main extraction line and a plurality of single extraction lines in a star structure;

FIG. 6: an apparatus in accordance with the invention with a line system comprising an extraction line with a plurality of extraction sectors arranged in series; and FIG. 7: a variant of an extraction port with a security against double use.

A first variant of an apparatus in accordance with the invention is shown in FIG. 1. It comprises a reception container in the form of a film bag 1 whose dimensions are such that a plurality of portions of approximately two liters of peritoneal dialysis solution in each case can be received.

The film bag 1 is implemented by a main extraction line 2 using a connection 3 having corresponding releasable connection partners, whereby the main extraction line 2 can be removed from the film bag 1.

A respective single extraction line 5a, 5b, etc. branches off from the main extraction line 2 at different branch points 4a, 4b, etc. that are distributed in series over the length of the main extraction line. Each of the single extraction lines has an extraction port 6a, 6b at its end and is furthermore provided with a clamp 7a, 7b, etc.

A main clamp 8 is provided in the main extraction line 2 between the branch point 4z closest to the bag and the connection element pair 3.

The single extraction ports 6 can be configured such as shown in FIG. 2 and can comprise a Y valve 9 to which the single extraction line 4 is fixedly connected and that has connectors for connecting a patient line 10 and a drainage line 11. The extraction port 6 can thus also be used for a draining procedure, with the valve 9 first being set after the connection of the patient line 10 and the drainage line 11 such that consumed dialysis solution flows out of the patient line 10 into the drainage line 11. The valve 9 can then be adjusted such that fresh dialysis solution can flow out of the single extraction line 4 into the patient line 10.

The individual extraction ports 6 can also be configured such as shown in FIG. 3 and can comprise a rotary switch 12 that can run through four positions. The rotary switch 12 is closed in position A. In position B, an outflow of consumed dialysis solution from the patient line 10 into the drainage line 11 is made possible. In position C, fresh dialysis solution can flow out of the single extraction line 4 into the patient line 10. In position D, the rotary switch is closed again. A turning of the switch 12 is only possible clockwise, whereby high operational safety is achieved.

In use of the apparatus shown in FIG. 1, provision can be made to use the extraction port 6a for the first liquid extraction that is seated at the last single extraction line 5a, i.e. at the extraction line furthest remote from the reception container. After ending this procedure, the respective single extraction line 6a can be closed using the clamp 7a. On the second liquid extraction, the second-to-last extraction port 6b can then be used and subsequently it can also be decoupled by closing the single extraction line 5b using the clamp 7b. This procedure can be repeated until the last extraction port 6z at the last single extraction line 5z, i.e. at the single extraction line closest to the reception container, is used or until the entire dialysis solution in the reception container has been used up.

Figures 4A, 4B:
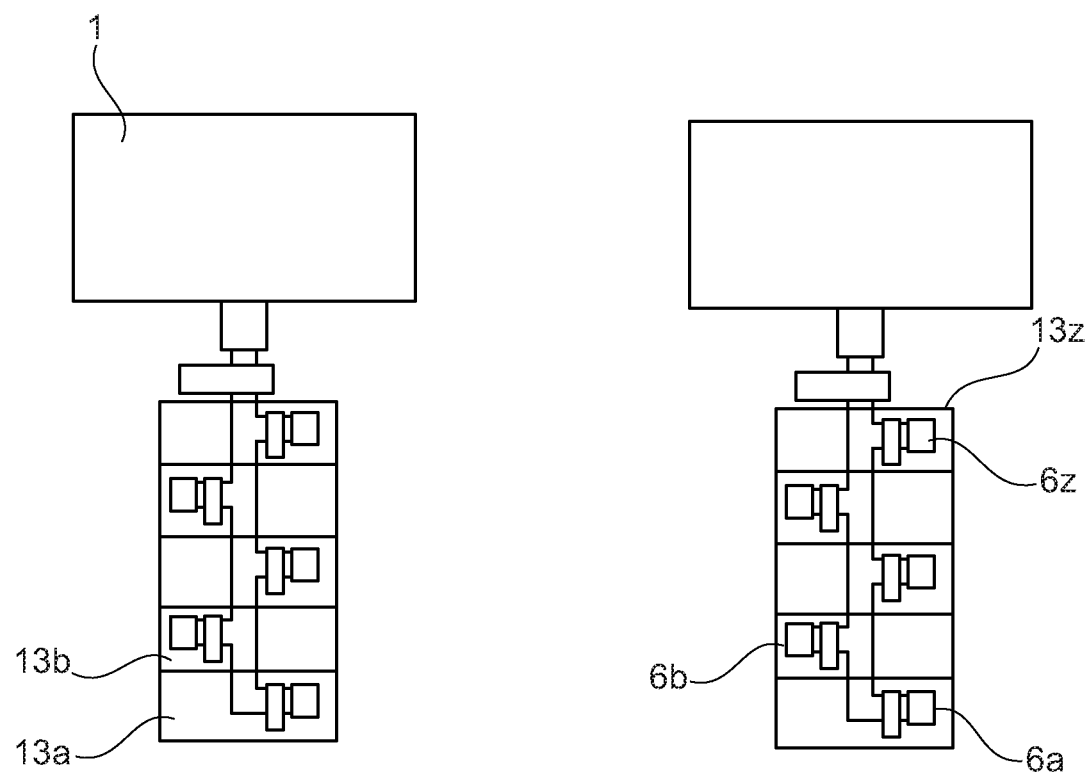

FIG. 4 shows a possibility of how the extraction ports 6a, 6b, etc. of the apparatus in accordance with FIG. 1 could be sealed in a manner such that the risk of confusing already used ports and fresh ports can be minimized. That is, a number of film sheaths 13a, 13b, etc. corresponding to the number of extraction ports 6a, 6b, etc. are provided that surround one another like Russian dolls. The innermost sheath 13z only surrounds the innermost extraction port 6z and each further sheath surrounds the existing sheath and a further extraction port. If the outermost sheath 13a, starting from the completely closed position of FIG. 4a, is opened by a user, the first extraction port 6a and the next sheath 13b are released that seals all the further extraction ports 6b, etc. If this next sheath 13b is opened, a further extraction port and the next-but-one sheath is released, as shown in FIG. 4b, and so on. The last extraction port 6z is only released after opening the innermost sheath 13z.

FIG. 5 shows a variant of the invention in which the main extraction line 2 opens into a distributor 14 and the single extraction lines 5a, 5b, etc. lead off from the distributor 14 in star shape. The distributor 14 has a rotary switch that is configured such that it can only be turned counterclockwise, as is indicated by an arrow in the Figure. A line is arranged in the drum of the rotary switch so that the release of only one individual single extraction line 5a, 5b, etc. is always possible. Due to the impossibility of a turning back clockwise, only such a single extraction line 5a, 5b, etc. can additionally only be released that has not yet been previously used. Although not shown in any more detail in the Figure, the single extraction lines are equipped with extraction ports and clamps, as was explained in more detail in connection with FIG. 1.

FIG. 6 shows a variant of the invention having a line system comprising an extraction line 15 having a plurality of extraction sectors 16a, 16b, etc. that are arranged in series and that are connected to one another using connectors 17a, 17b, etc. The extraction line 15 is connected at its end at the right in FIG. 6 to the solution bag, such as was explained in connection with FIG. 1 for the main extraction line. The connectors 17a, 17b, etc. each comprise extraction ports 6a, 6b, etc. which are configured as explained in connection with FIG. 2. The connectors 17a, 17b, etc. furthermore comprise a respective break point 18a, 18b, etc. each to be able to decouple the extraction sectors 16a, 16b, etc. having used extraction ports 6a, 6b, etc. For example, the connector 17b can be cut at the break point 18b once the extraction port 6a had been used for a treatment and this use had been ended. The cutting of the connection at the break points 18a, 18b, etc. can generally take place in any desired manner such as by breaking, with the break points 18a, 18b, etc. preferably being configured such that on the decoupling, the line leading to the decoupled sector is closed to prevent an outflow of fresh dialysis solution.

A sealing of the extraction ports 6a, 6b, etc. can also take place in the variants of FIGS. 5 and 6 such as was explained in connection with FIG. 4 for the variant of FIG. 1.

Figure 7A:
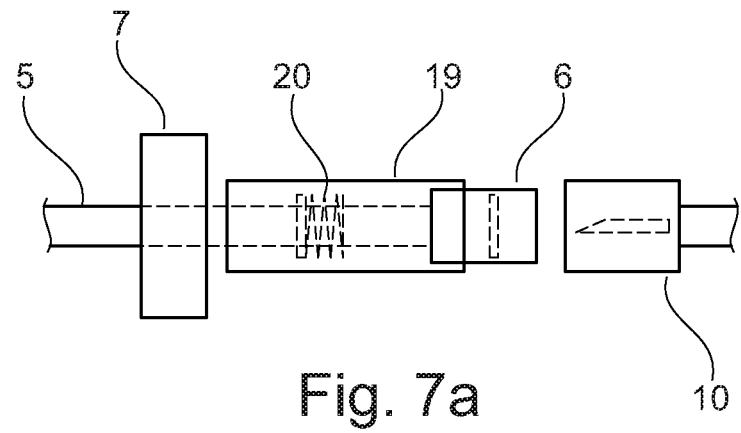
Figure 7B:
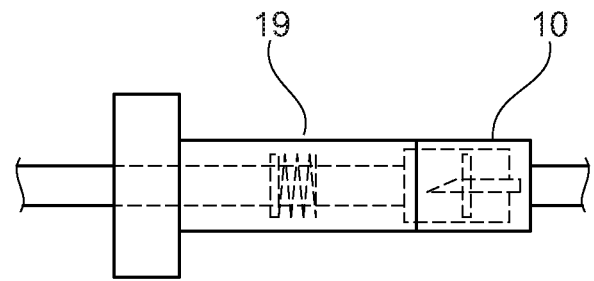
Figure 7C:
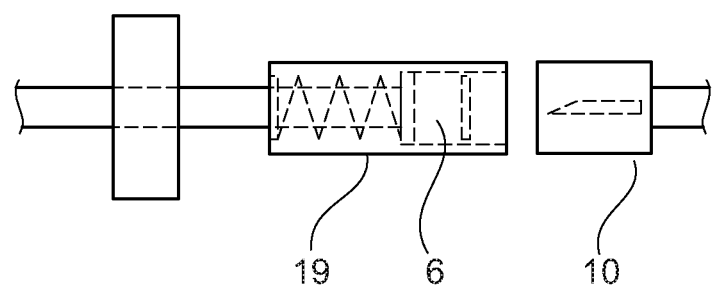

Finally, FIG. 7 shows a possible embodiment of the extraction ports 6 having a sleeve 19 for avoiding a use of an already used port. The sleeve 19 is configured such that it can be pushed in an axial direction of the port 6 from an open position shown in FIG. 7a into a closed position shown in FIG. 7c, with the extraction port 6 being blocked in the closed position. The closed position is irreversible since the sleeve 19 has a latch nose that is not shown in any more detail in the Figure and that comes to lie in the closed position behind, or in the Figure to the right of a latch projection likewise not shown in any more detail in the Figure. The sleeve 19 is preloaded by a spring 20 against the closed position. If a patient line 10 is plugged onto the port 6, the sleeve is pressed to the rear or to the left in the Figure into a position that is shown in FIG. 7b. A retaining bridge is broken open here which is not shown in any more detail in the Figure and had previously, i.e. in the state of FIG. 7a, held the sleeve 19 against the preload in its open position. As long as the patient line 10 remains at the port 6, as shown in FIG. 7b, the sleeve 19 is held in this position. On the removal of the patient line 10 from the port 6, the sleeve 19 is then pressed by the spring 20 to the right into the position shown in FIG. 7c and closes irreversibly.

The invention claimed is:

1. An apparatus containing a dialysis solution or a dialysis solution concentrate, useful in peritoneal dialysis, comprising a reception container that can accommodate a solution volume which is intended for at least two treatments, characterized in that the apparatus has a plurality of extraction ports for extracting the dialysis solution or the dialysis solution concentrate from the reception container and the extraction ports are individually sealed by airtight sheaths, with provision being made that a number of sheaths corresponding to the number of extraction ports is present, with an innermost sheath surrounding an extraction port.

2. An apparatus in accordance with claim 1, characterized in that a valve and a drainage port are associated with each extraction port.

3. An apparatus in accordance with claim 1, characterized in that the apparatus has a main extraction line connected to the reception container and from which a plurality of single extraction lines having the extraction ports lead off.

4. An apparatus in accordance with claim 3, characterized in that respective closing means by which the single extraction lines can be closed are arranged in the single extraction lines.

5. An apparatus in accordance with claim 4, characterized in that the closing means are configured such that they close automatically on or after a decoupling of the single extraction line from a patient.

6. An apparatus in accordance with claim 3, characterized in that the single extraction lines branch off from the main extraction line at different branch points that are distributed over a length of the main extraction line.

7. An apparatus in accordance with claim 6, characterized in that respective closing means are arranged in the main extraction line between branch points of the single extraction lines that follow one another and with which the main extraction line can be closed.

\* \* \* \* \*